US009085752B2

(12) United States Patent
Oura et al.

(10) Patent No.: US 9,085,752 B2
(45) Date of Patent: Jul. 21, 2015

(54) ATMOSPHERE CONTROL COMPOSITION

(75) Inventors: Ayako Oura, Matsudo (JP); Shigeki Imagawa, Tokyo-to (JP); Makoto Yoshizawa, Tokyo-to (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 0 days.

(21) Appl. No.: 13/511,772

(22) PCT Filed: Nov. 24, 2010

(86) PCT No.: PCT/JP2010/070891
§ 371 (c)(1),
(2), (4) Date: Jun. 12, 2012

(87) PCT Pub. No.: WO2011/065363
PCT Pub. Date: Jun. 3, 2011

(65) Prior Publication Data
US 2012/0282690 A1 Nov. 8, 2012

(30) Foreign Application Priority Data

Nov. 24, 2009 (JP) ................................. 2009-266276
Nov. 24, 2009 (JP) ................................. 2009-266277

(51) Int. Cl.
*C12N 5/00* (2006.01)
*C12M 1/34* (2006.01)
*C12M 1/00* (2006.01)

(52) U.S. Cl.
CPC ............. *C12M 41/34* (2013.01); *C12M 29/26* (2013.01); *C12N 5/0018* (2013.01); *C12N 2500/24* (2013.01); *C12N 2500/30* (2013.01); *C12N 2500/38* (2013.01)

(58) Field of Classification Search
None
See application file for complete search history.

(56) References Cited

U.S. PATENT DOCUMENTS

| 5,914,070 | A | * | 6/1999 | Araki et al. | ............... | 252/188.28 |
| 6,114,162 | A | | 9/2000 | Kashiba | | |
| 2002/0064875 | A1 | * | 5/2002 | Chen et al. | ..................... | 435/399 |
| 2006/0160848 | A1 | * | 7/2006 | Burcham et al. | ............... | 514/310 |

FOREIGN PATENT DOCUMENTS

| CN | 1442454 A | 9/2003 |
| CN | 101386836 A | 3/2009 |
| CN | 101537307 A | 9/2009 |
| EP | 0111583 A1 | 6/1984 |
| EP | 0 869 172 A2 | 10/1998 |
| JP | 62-40273 A | 2/1987 |
| JP | 5-13200 U | 2/1993 |
| JP | 05-140138 A | 6/1993 |
| JP | 3034364 U | 11/1996 |
| JP | 9-252766 A | 9/1997 |
| JP | 10-314581 A | 12/1998 |
| JP | 10-327845 A | 12/1998 |
| JP | 3021148 B2 | 3/2000 |
| JP | 2004-049297 A | 2/2004 |
| JP | 3806374 B2 | 8/2006 |
| JP | 2009-095315 A | 5/2009 |
| JP | 2009-291166 A | 12/2009 |
| WO | 99/27010 A1 | 6/1999 |
| WO | 2007/091223 A1 | 8/2007 |

OTHER PUBLICATIONS

Sigma-Aldrich Medium 199 Formulation brochure, obtained from the internet: http://www.sigmaaldrich.com/life-science/cell-culture/learning-center/media-formulations/medium-199.html.*
Chinese Office Action dated Jan. 15, 2013, issued against Chinese Application 201080053258.8.
Chinese Office Action issued Sep. 23, 2013 with English language translation.
International Search Report dated Dec. 28, 2010, corresponding with JP International Application No. PCT/JP2010/070891.
International Preliminary Report on Patentability and Written Opinion, issued in PCT/JP2010/070891, Jun. 21, 2012.
JP 2009-291166 (translation), Dec. 17, 2009.
JP 3034364 Y1 (translation), May 2, 1998.
JP 05-13200 U (translation) Feb. 23, 1993.

* cited by examiner

*Primary Examiner* — Allison Fox
*Assistant Examiner* — Yvonne Pyla
(74) *Attorney, Agent, or Firm* — Fitch, Even, Tabin & Flannery, LLP

(57) ABSTRACT

The atmosphere control composition according to the present invention is an atmosphere control composition for use in the culture of cells, which comprises (a) an ascorbic acid component, (b) water, (c) a porous carrier, (d) an aldehyde-removing agent, (e) a transition metal catalyst and/or an alkaline earth metal hydroxide, wherein the aldehyde-removing agent comprises at least one component selected from the group consisting of ethylene urea, urea, arginine, lysine hydrochloride and a polyallylamine. According to the present invention, the atmosphere control composition feasible for preventing the generation of aldehyde can be provided without affecting the oxygen absorption ability and the carbon dioxide generation ability thereof.

13 Claims, No Drawings

ATMOSPHERE CONTROL COMPOSITION

CROSS-REFERENCE TO RELATED APPLICATION

This Application is a U.S. National Phase Application filed under 35 U.S.C §371 of International Application No. PCT/JP2010/070891, filed Nov. 24, 2010, designating the United States, the complete disclosure of which is incorporated by reference.

This application is based upon and claims the benefit of priority from the prior Japanese Patent Application Nos. 2009-266276 (filed on Nov. 24, 2009) and 2009-266277 (filed on Nov. 24, 2009), the entire contents of which are incorporated herein by reference.

TECHNICAL FIELD

The present invention relates to an atmosphere control composition having the aldehyde-removing ability and to an atmosphere control package which comprises packaging the composition with a gas permeable packaging material. The present invention also relates to a method for culturing cells with use of the package.

BACKGROUND ART

A gas atmosphere different from air atmosphere is required in the culture of biological samples such as tissues and cells conducted in the fields of the research or industry of biology, generation and biotechnology. Generally in the culture of cells, the cells in the culture fluid must be maintained at an appropriate temperature, and the culture fluid must be maintained at a constant pH as well. In the case of a culture fluid with the generally used pH buffer system of carbon dioxide—sodium hydrogen carbonate, carbon dioxide is required to be in the concentration of about 5% by volume in order to maintain pH 7.4.

In addition, the low oxygen culture of cells has recently attracted attention in many research fields. Specifically, the effects of deriving genes such as hypoxia inducible factor (HIF) in connection with biochemical reactions similar to in vivo reactions or angiogenesis and promoting the proliferation and differentiation of cells have been confirmed by the cell culture conducted under hypoxic atmosphere similar to that of a living body. Also, in the ischemia reperfusion experiment models which reproduce organ dysfunction due to blood stagnation, intracellular mechanisms have been studied in detail by exposing the cells or tissues under an anoxic condition for a certain period. Furthermore, in the drug sensitivity test with use of human cells, drug metabolism tests have been carried out by producing reducing atmosphere under an anoxic condition.

In the cultures of the biological samples described above, a given gas atmosphere is produced with a carbon dioxide incubator or a multigas incubator (referred to hereinafter as "carbon dioxide gas incubators") and cell culture is conducted in a breathable culture vessel held in the carbon dioxide gas incubators. In this connection, multiwell plates, flasks, petri dishes, chamber slides, culture bags and the like are generally used as the culture vessel.

The parallel treatment of plural samples always involves some risk of the contamination (cross contamination) of the different sample. Coexistence of many samples within carbon dioxide gas incubators is apprehensive for the increased risk of cross contamination. Thus, carbon dioxide gas incubators having plural sample chambers have been developed, but installation of these incubators is limited due to their expensiveness. Moreover, introduction of the carbon dioxide gas incubators may be limited because of the problem with the management of high pressure gases.

For the reasons described above, a method for forming a certain gas atmosphere by using an airtight container and an atmosphere control agent to be injected into the container is also used in place of the carbon dioxide gas incubators. So far, atmosphere control agents comprising water and sodium borohydride as the main ingredients had been used in many cases of anaerobic culture and microaerophilic culture with an atmosphere control agent. The main current of the atmosphere control agent has been transferred into the products containing ascorbic acid as the main ingredient from the viewpoint of safety and reliability.

The oxygen absorbent containing the ascorbic acid components as the main ingredient can be prepared, for example, by mixing an ascorbic acid component, a metal salt, activated carbon and water as disclosed in Japanese Patent Laid-Open Publication No. H10-314581 (lit. 1). In addition, it is possible to control not only the amount of carbon dioxide to be generated but also the concentration of carbon dioxide in a container having a fixed volume by adding an alkaline earth metal hydroxide to the oxygen absorbent as disclosed in Japanese Patent Laid-Open Publication No. H10-327845 (lit. 2). Furthermore, Japanese Patent Laid-Open Publication No. H09-252766 (lit. 3) discloses that an atmosphere control agent which may form the appropriate concentrations of oxygen and carbon dioxide depending on the biological materials has been developed and used.

In the field of conserving foods with an atmosphere control agent, it is known that acetaldehyde generates with the deterioration of foods or by the oxidation of ethanol in the use of an iron type oxygen scavenger in combination with ethanol, and an oxygen scavenger having the acetaldehyde-removing ability has been developed in order to remove acetaldehyde (Japanese Patent Laid-Open Publication No. S62-40273 (lit. 4). However, when no aldehyde generates from an object for preservation and an atmosphere control agent and ethanol are not used in combination, it has not been known that aldehyde will generate with the use of an atmosphere control agent. Furthermore, in the field of cell culture with an atmosphere control agent, no examination has been done on the effect of aldehyde on the cell culture so far as the present inventors know.

The present applicant has hitherto proposed in the field of the cell culture a method for adjusting the atmosphere of a low oxygen concentration as described, for example, in Japanese Patent Laid-Open Publication No. H09-0252766.

SUMMARY OF THE INVENTION

The present inventors have now found out the following.

It has been found that even if the gas impermeable container is maintained at the gas atmosphere which may be appropriate to the cell culture with the atmosphere control agent described above and the cell culture is conducted in the container, the result of the culture may be deteriorated as compared with the cell culture by realizing the carbon dioxide gas atmosphere with use of the carbon dioxide gas incubators. For instance, in the atmosphere control agents described in lits. 1 to 3, trace amount of by-products may be generated with the absorption of oxygen, and such a trace amount of by-products which will produce no effect on general objects of preservation may have an effect upon the growth of the intended biological species. Thus, the present inventors have earnestly investigated and examined the cause of the deteriorated culture result and found that the deterioration is caused by the influence of a by-product derived from an atmosphere control agent. Moreover, the present inventors have advanced the investigation and examination and unexpectedly found that the by-product is an aldehyde.

As the result of the earnest investigation and examination, the present inventors have succeeded in suppressing the generation of aldehydes without affecting the oxygen absorption ability and the carbon dioxide generation ability inherently existing in an atmosphere control agent by combining a specific aldehyde-removing agent with the atmosphere control agent.

The present invention is based on such information described above.

Therefore, the present invention aims at providing an atmosphere control composition which suppresses the generation of by-products, an atmosphere control package and a method for culturing cells with use of the package.

That is, the present invention relates to an atmosphere control composition for use in the culture of cells comprising
(a) an ascorbic acid component,
(b) water,
(c) a porous carrier,
(d) an aldehyde-removing agent, and
(e) a transition metal catalyst and/or an alkaline earth metal hydroxide
wherein the aldehyde-removing agent is ethylene urea, urea, arginine, lysine hydrochloride or a polyallylamine.

According to the first preferred embodiment of the present invention, the atmosphere control composition of the present invention comprises a transition metal catalyst and at least two alkaline earth metal hydroxides as the ingredient (e).

In the first embodiment described above, the alkaline earth metal hydroxides to be used are more preferably magnesium hydroxide and calcium hydroxide.

In the first embodiment described above, the atmosphere control composition of the present invention further preferably comprises
100 parts by mass of an ascorbic acid component as the ingredient (a),
100 to 200 parts by mass of water as the ingredient (b),
50 to 400 parts by mass of a porous carrier as the ingredient (c),
0.5 to 25 parts by mass of an aldehyde-removing agent as the ingredient (d), and
5 to 25 parts by mass of a transition metal catalyst, 1 to 10 parts by mass of magnesium hydroxide and 20 to 40 parts by mass of calcium hydroxide as the ingredient (e),
wherein the oxygen concentration in a gas impermeable airtight container may be adjusted to the range of 0.1% by volume or less and the carbon dioxide concentration to the range of 2 to 10% by volume by housing said composition into said airtight container.

According to the second preferred embodiment of the present invention, the atmosphere control composition of the present invention comprises only the alkaline earth metal hydroxides as the ingredient (e).

In the second embodiment described above, the atmosphere control composition of the present invention comprises
100 parts by mass of an ascorbic acid component as the ingredient (a),
100 to 200 parts by mass of water as the ingredient (b),
50 to 400 parts by mass of a porous carrier as the ingredient (c),
0.5 to 25 parts by mass of an aldehyde-removing agent as the ingredient (d), and
20 to 55 parts by mass of an alkaline earth metal hydroxide as the ingredient (e),
wherein the oxygen concentration in a gas impermeable airtight container may be adjusted to the range of 1 to 7% by volume and the carbon dioxide concentration to the range of 2 to 10% by volume by housing said composition into said airtight container.

According to the third preferred embodiment of the present invention, the atmosphere control composition of the present invention comprises a transition metal catalyst as the ingredient (e) and further a carbonate salt as the ingredient (f).

In the third embodiment described above, the atmosphere control composition of the present invention comprises
100 parts by mass of an ascorbic acid component as the ingredient (a),
100 to 200 parts by mass of water as the ingredient (b),
50 to 400 parts by mass of a porous carrier as the ingredient (c),
0.5 to 25 parts by mass of an aldehyde-removing agent as the ingredient (d),
5 to 25 parts by mass of a transition metal catalyst as the ingredient (e), and
10 to 70 parts by mass of a carbonate salt as the ingredient (f),
wherein the oxygen concentration in a gas impermeable airtight container may be adjusted to 12 to 18% by volume and carbon dioxide concentration to 2 to 10% by volume by housing said composition into said airtight container.

The combination of the transition metal catalyst or the carbonate salt has an advantage that the progression of the oxidation reaction can be promoted. The composition combined with the alkaline earth metal hydroxide has an advantage over the one combined with no alkaline earth metal hydroxide in that the carbon dioxide concentration is regulated more easily by the atmosphere control agent.

According to one more preferred embodiment of the present invention, the atmosphere control composition according to the present invention further comprises a thermoplastic resin.

Moreover, in the atmosphere control composition of the present invention, the porous carrier as the foregoing ingredient (c) is preferably activated carbon.

In this case, the activated carbon has an advantage in that the absorbing powder of oxygen of the atmosphere control composition can be enhanced owing to the large heat reserving ability and specific surface area of the activated carbon.

The present invention also relates to an atmosphere control package which comprises packaging the foregoing atmosphere control composition with a packaging material totally or partly containing an air permeable packaging material.

According to the atmosphere control composition and the atmosphere control package of the present invention, it becomes possible to suppress the generation of aldehydes without affecting the oxygen absorption ability and the carbon dioxide generation ability inherently existing in the atmosphere control agent and to culture efficiently with a simple and easy operation a biological sample of which growth is inhibited by the presence of aldehyde, for example, cells.

Moreover, the present invention relates to a method for culturing cells which comprises setting up the atmosphere control package described above and a culture vessel having cells and a culture medium housed therein within a gas impermeable airtight container and thus culturing the cells by adjusting the carbon dioxide concentration in said airtight container to the range of 2 to 10% by volume. In this connection, the concentration of aldehyde fused into the culture medium is preferably adjusted to the range of 2 mg/l or less.

Furthermore, the other embodiments of the present invention include the followings:

(1) an atmosphere control composition containing an ascorbic acid component, a transition metal catalyst, water, a porous carrier and ethylene urea;

(2) the atmosphere control composition described in (1) which contains further a carbonate salt or an alkaline earth metal hydroxide;

(3) the atmosphere control composition containing an ascorbic acid component, a transition metal catalyst, water, a porous carrier and an aldehyde-removing agent, wherein the aldehyde-removing agent is urea, arginine, lysine hydrochloride or a polyallylamine; and (4) the atmosphere control composition described in (3) which contains further a carbonate salt or an alkaline earth metal hydroxide.

According to this method for culturing cells, it will be possible to actualize a gas atmosphere containing the carbon dioxide concentration in the range of 2 to 10% by volume within an airtight container with the aid of an atmosphere control package without use of apparatuses such as carbon dioxide gas incubators which can be hardly purchased or introduced with ease. Thus, according to the present invention, it becomes possible to provide a gas atmosphere for culturing cells inexpensively with a simple and easy operation, and the culture result equivalent to that with use of carbon dioxide gas incubators can be obtained without the deterioration of the culture results because aldehyde as the by-product is suppressed in the package. Thus, the atmosphere control agent of the present invention makes possible the simple and economical cell culture by which the result of culturing cells equivalent to that with use of carbon dioxide gas incubators can be obtained.

According to the present invention, it is possible to provide an atmosphere control composition which can suppress the generation of aldehyde without affecting the oxygen absorption ability and the carbon dioxide generation ability inherently existing in the atmosphere control agent, an atmosphere control package and a method for culturing cells with the atmosphere control agent. The suppression of the generation of aldehyde in the atmosphere for culturing cells may be led to the suppression of the inhibition of the cell culture by the aldehyde in the cell culture, and the culture can be carried out advantageously.

DETAILED DESCRIPTION OF THE INVENTION

[Atmosphere Control Composition]

The atmosphere control composition according to the present invention is now described in detail.

That is to say, the atmosphere control composition according to the present invention comprises as described above (a) an ascorbic acid component,
(b) water,
(c) a porous carrier,
(d) an aldehyde-removing agent, and
(e) a transition metal catalyst and/or an alkaline earth metal hydroxide and is used for cell culture.

(a) Ascorbic Acid Component

An ascorbic acid component is combined as an oxygen absorbing ingredient in the atmosphere control composition of the present invention. The ascorbic acid component means L-ascorbic acid and stereoisomers thereof, and salts and hydrates thereof such as L-ascorbic acid, sodium L-ascorbate, calcium L-ascorbate, sodium D-iso-ascorbate, and the like. As the ascorbic acid component, it is possible to use the foregoing compounds in a simple substance or a mixture. In addition, it is desirable from the viewpoint of the absorbing powder of oxygen that the ascorbic acid component is dissolved in water to give a solution, which is impregnated into a porous carrier such as activated carbon before combining with the atmosphere control composition. On this occasion, the ascorbic acid component is desirably regulated to a concentration as near as possible to its saturated solubility because the higher concentration of the aqueous ascorbic acid component can make the lesser amount of the porous carrier used. Thus, it is desirable to select as the ascorbic acid component a compound having a higher solubility to water specifically sodium L-ascorbate. When sodium L-ascorbate is used, the concentration of the aqueous solution is appropriately adjusted to the range of 40 to 55% by mass.

In the atmosphere control agent, the oxygen concentration is regulated by taking advantage of the oxidation reaction of the ascorbic acid component to absorb oxygen in the atmosphere, and the carbon dioxide concentration in the atmosphere is also regulated by taking advantage of the generating carbon dioxide. In this connection, carbon dioxide equimolar to the oxygen molecule consumed is produced in the oxidation reaction. While the carbon dioxide concentration will be increased with the decrease of the oxygen concentration owing to the principle described above, the increase of the carbon dioxide may also be suppressed by combining a compound having the carbon dioxide absorbing ability such as an alkaline earth metal hydroxide with the atmosphere control composition. In contrast with this, it is also possible to generate carbon dioxide in half or more of the decreased amount of oxygen by combining a compound having the carbon dioxide generating ability with the atmosphere control composition. Thus in the atmosphere control agent of the present invention, the specific atmosphere may be adjusted to the desired oxygen-carbon dioxide concentration by appropriately selecting the ingredients and blending quantities of the atmosphere control composition to regulate the progress of the oxidation reaction and the amount of carbon dioxide generated in the reaction.

(b) Water

Water is added to the atmosphere control composition of the present invention as an essential to the progress of the oxidation reaction of the ascorbic acid component. The amount of water added to the atmosphere control composition is preferably in the range of 100 to 200 parts by mass water to 100 parts by mass of the ascorbic acid component, more preferably in the range of 110 to 180 parts by mass, and further preferably in the range of 120 to 180 parts by mass. In these ranges, the oxygen absorption by the atmosphere control composition can be further expedited in comparison with the ranges other than those described above. When water is added to the composition, it is desirable to impregnate the water into a porous carrier described hereunder from the viewpoint that the composition can be prepared as a solid having fluidity. Furthermore, soluble ingredients including ascorbic acid component dissolved in water may be added to the composition, and insoluble ingredients may be dispersed in water as well.

(c) Porous Carrier

A porous carrier is combined with the atmosphere control composition of the present invention. The porous carrier has a function as a carrier for impregnating water as described above. The porous carrier includes, for example, activated carbon, diatomaceous earth, silica gel, zeolite, pearlite, calcium silicate, pumice, cellulose, activated clay, alumina, hydroxyapatite, porous resins, porous glass and the like, and among others activated carbon is preferred.

The amount of the porous carrier added to the atmosphere control composition is preferably in the range of 50 to 400 parts by mass to 100 parts by mass of the ascorbic acid component, more preferably in the range of 75 to 300 parts by mass. In these ranges, the repletion of the atmosphere control composition can be further enhanced in comparison with the ranges other than those described above because of the improved fluidity.

If activated carbon is used as the porous carrier, the oxidation reaction may be promoted owing to the heat storage ability. In addition, if an aqueous solution of an ascorbic acid component is impregnated into activated carbon to prepare an atmosphere control composition, it is possible to increase the contact area with air due to the specific area of the composition and further to promote the oxidation reaction. As the activated carbon, the ones produced by using various methods including the steam activation of sawdust, coal or coconut shells as the raw materials or the drug activation of zinc chloride and the like can be used. Among others, the particulate activated carbon having a particle diameter in the range 0.1 mm to 2 mm, preferably in the range of 0.5 to 1 mm is desirable because of its excellent fluidity.

(d) Aldehyde-removing Agent

To atmosphere control composition of the present invention is added an aldehyde-removing agent in order to remove aldehyde produced as the byproduct with the progress of the oxidation reaction of the ascorbic acid component. The compound having the aldehyde-removing ability includes well known compounds such as amines, but preferably ethylene urea, urea, arginine, lysine hydrochloride or a polyallylamine which has the satisfactory aldehyde-removing ability with no generation of irritant odor and exhibits strong effect with a small amount is added, and more preferably ethylene urea showing a strong effect with a smaller amount is added.

The aldehyde described herein means a compound having at least one formyl group within the molecule, that is, an aldehyde. The aldehyde in the present invention typically means the one which is produced as a byproduct in the course of oxygen absorption or cell culture, and the aldehyde includes any one which is classified into aldehydes in the chemical field as far as they adversely affect the cell culture. Specifically, the aldehyde includes for example formaldehyde, acetaldehyde and the like.

As the method for adding the aldehyde-removing agent into the gas impermeable airtight container, any method may be selected including a method for adding a package having an aldehyde-removing agent filled therein as a package different from the atmosphere control agent into the container, a method for directly adding the aldehyde-removing agent as a solid to the atmosphere control agent, and a method for dissolving aldehyde-removing agent together with the ascorbic acid component in water to make an aqueous solution, which is impregnated into a porous carrier before mixing with the atmosphere control composition, but the method for impregnating the solution into the porous carrier before mixing with the atmosphere control agent from the standpoint of economy and dispersibility. In this case, it is desirable to add the aldehyde-removing agent in a lesser amount within the range that the agent can exhibit the desired effects on taking account of the factors such as the solubilities of the aldehyde-removing agent and the ascorbic acid in water, the viscosity of the aqueous solution, the blended amount of water and the porous carrier, the fluidity of the porous carrier having the aqueous solution impregnated therein and the economy.

The blended amount of the aldehyde-removing agent is preferably in the range of 0.5 to 25 parts by mass to 100 parts by mass of the ascorbic acid component, more preferably in the range of 1.0 to 10 parts by mass, further preferably in the range of 1.0 to 5.0 parts by mass. In this case, the aldehyde-removing ability of the atmosphere control composition can be further improved and the economy can also be enhanced as compared with the case that the blended amount is out of the range described above.

In the method for culturing cells of the present invention, when an open-ended container having 10 ml of distilled water received therein is placed in the gas impermeable airtight container, the concentration of aldehyde transferred into the distilled water during the period of culture is preferably in the range of 2.0 mg/l or less, more preferably in the range of 1.5 mg/l or less, further preferably in the range of 1 mg/l or less.

(e) Transition Metal Catalyst and/or Alkaline Earth Metal Hydroxide

The atmosphere control composition of the present invention further comprises as the ingredient (e) a transition metal catalyst and/or an alkaline earth metal hydroxide. In this connection, the transition metal catalyst and/or the alkaline earth metal hydroxide include all cases of containing both the transition metal catalyst and the alkaline earth metal hydroxide, only the transition metal catalyst, and only the alkaline earth metal hydroxide.

Transition Metal Catalyst

To the atmosphere control composition of the present invention is blended a transition metal catalyst for promoting the oxidation reaction of the ascorbic acid component, if necessary. The transition metal catalyst is a catalyst having metal compounds such as the salts or oxides of transition metals. The transition metals such as iron, manganese, zinc, copper and cobalt are suitably used. The transition metals include the halides and mineral acids of the transition metals, for example, the chlorides and sulfates of the transition metals. Typically, the anhydrides or hydrates of ferrous chloride, ferric chloride, ferrous sulfate, ferric sulfate, manganese chloride, zinc sulfate, copper sulfate, copper chloride and cobalt sulfate may be enumerated, and among others, the hydrate of ferrous sulfate is preferred. On the other hand, the effect for promoting the oxidation reaction by the transition metal catalyst is not conspicuous immediately after the initiation of the reaction and shows an increasing trend from several hours after the initiation of the reaction. Thus, if low oxygen atmosphere is intended to be maintained, the aimed oxygen concentration can be maintained more stably by controlling the blended amount of the transition metal catalyst.

The amount of the transition metal catalyst blended into the atmosphere control composition is preferably in the range of 5 to 25 parts by mass to 100 parts by mass of the ascorbic acid component, more preferably in the range of 10 to 20 parts by mass. In this case, the oxygen absorbing rate of the atmosphere control composition can be further promoted as compared with the case that the blended amount is out of the range described above.

Alkaline Earth Metal Hydroxide

In the atmosphere control composition of the present invention, an alkaline earth metal hydroxide having the carbon dioxide absorbing ability can be used, if necessary, for adjusting the carbon dioxide concentration. Particularly, calcium hydroxide, magnesium hydroxide or a mixture thereof can be suitably used. The alkaline earth metal hydroxide having an average particle diameter in the range of 1 to 100 µm is preferably used, and the alkaline earth metal hydroxide having an average particle diameter in the range of 2 to 50 µm is more preferably used. The amount of the alkaline earth metal hydroxide is preferably blended in the range of 20 to 120 parts by mass to 100 parts by mass of the ascorbic acid component. In this case, the composition can be finished to the one having good fluidity and suitable for packages as compared with the case that the blended amount is out of the range described above. In addition, when it is intended to absorb a large amount of carbon dioxide in a short time, an alkaline earth metal hydroxide such as calcium hydroxide having a high solubility in water and a high carbon dioxide absorbing rate is suitably used. Moreover, the generated amount of carbon dioxide is not constant and varies every moment. For instance, in the further rapid formation of a gas atmosphere having 0% of the oxygen concentration and 5% of the carbon dioxide concentration, a large amount of carbon dioxide is generated at once immediately after the initiation of the reaction because of the absorption of all oxygen in the atmosphere at a time and the generated amount of carbon dioxide is subsequently decreased rapidly. In such cases, calcium hydroxide having a high carbon dioxide absorbing rate and magnesium hydroxide having a low carbon dioxide absorbing rate are preferably blended. The blended amounts on that occasion are preferably in the range of 1 to 10 parts by mass, more preferably 2 to 6 parts by mass of magnesium hydroxide to 100 parts by mass of the ascorbic acid component, and preferably 20 to 40 parts by mass, more preferably 25 to 35 parts by mass of calcium hydroxide to 100 parts by mass of the ascorbic acid component. In this case, the carbon dioxide concentration can be maintained in the range of 5±1%. In this connection, the combination of the alkaline earth metal hydroxide and the carbonate salt is unfavorable, because it is difficult to control the carbon dioxide concentration.

(f) Carbonate Salt

To the atmosphere control composition of the present invention can be added a carbonate salt which controls and maintain the reaction in an alkaline range in order to advance the reaction rapidly. The carbonate salt includes preferably water soluble carbonates such as sodium carbonate, sodium hydrogen carbonate, hydrates of sodium carbonate and the like. The blended amount of the carbonate salt is preferably in the range of 10 to 120 parts by mass to 100 parts by mass of an ascorbic acid component, more preferably in the range of 10 to 70 parts by mass, particularly in the range of 50 to 60 parts by mass.

(g) Thermoplastic Resin

To the atmosphere control composition of the present invention can be blended a thermoplastic resin to the atmosphere control agent in order to suppress the overheating of the atmosphere control composition with the progress of the oxygen absorbing reaction. The thermoplastic resin to be used is a granular material preferably having a particle diameter in the range of 1 to 500 μm, and more preferably in the range of 10 to 300 μm from the viewpoint of the miscibility with the other compositions. In addition, the softening point of the thermoplastic resin is in the range of 90 to 125° C. In this case, overheating can be suppressed more effectively as compared with the case that the softening point is out of the range described above. The kind of the thermoplastic resin is not specifically limited, but polyethylene, polypropylene, an ethylene-vinyl acetate copolymer, an elastomer, or a mixture thereof can be exemplified, and particularly the low molecular weight polyethylene, polypropylene or the mixture thereof having a molecular weight of 10000 or less is appropriately used from the standpoint of the easiness of controlling the softening point and low influence of the odor.

The blended amount of the thermoplastic resin is preferably in the range of 35 to 300 parts by mass to 100 parts by mass of the ascorbic acid component.

First Embodiment

The first embodiment of the atmosphere control composition of the present invention comprises, as described above, as the ingredient (e) the transition metal catalyst and at least two alkaline earth metal hydroxides in the atmosphere control composition of the present invention. More preferably, the alkaline earth metal hydroxides comprise magnesium hydroxide and calcium hydroxide.

Further preferably, in the first embodiment described above, the atmosphere control composition of the present invention comprises 100 parts by mass of the ascorbic acid component as the ingredient (a), 100 to 200 parts by mass, preferably 110 to 180 parts by mass of water as the ingredient (b), 50 to 400 parts by mass, preferably 75 to 300 parts by mass, more preferably 100 to 130 parts by mass of the porous carrier as the ingredient (c), 0.5 to 25 parts by mass, preferably 1.0 to 10 parts by mass, more preferably 1.0 to 5.0 parts by mass of the aldehyde-removing agent as the ingredient (d), and 5 to 25 parts by mass, preferably 10 to 20 parts by mass of the transition metal catalyst, 1 to 10 parts by mass, preferably 2 to 6 parts by mass of magnesium hydroxide, 20 to 40 parts by mass, preferably 25 to 35 parts by mass of calcium hydroxide as the ingredient (e), wherein the oxygen concentration in a gas impermeable airtight container may be adjusted to the range of 0.1% by volume or less and the carbon dioxide concentration to the range of 2 to 10% by volume by housing said composition into said airtight container. Here, the carbon dioxide concentration to be controlled in the airtight container is preferably in the range of 3 to 8% by volume, more preferably 5±1% by volume.

At this point, when the atmosphere control composition of the first embodiment further comprises the thermoplastic resin, the blended amount is preferably in the range of 35 to 300 parts by mass to 100 parts by mass of the ascorbic acid component, and more preferably in the range of 70 to 150 parts by mass.

Second Embodiment

The second embodiment of the atmosphere control composition of the present invention comprises, as described above, as the ingredient (e) only the alkaline earth metal hydroxide.

More preferably, the atmosphere control composition of the present invention in the second embodiment described above comprises 100 parts by mass of the ascorbic acid component as the ingredient (a), 100 to 200 parts by mass, preferably 110 to 180 parts by mass of water as the ingredient (b), 50 to 400 parts by mass, preferably 75 to 300 parts by mass, more preferably 85 to 120 parts by mass of the porous carrier as the ingredient (c), 0.5 to 25 parts by mass, preferably 1.0 to 10 parts by mass, more preferably 1.0 to 5.0 parts by mass of the aldehyde-removing agent as the ingredient (d), and 20 to 55 parts by mass, preferably 35 to 45 parts by mass of the alkaline earth metal hydroxide as the ingredient (e), wherein the oxygen concentration in a gas impermeable airtight container may be adjusted to the range of 1 to 7% by volume and the carbon dioxide concentration to the range of 2 to 10% by volume by housing said composition into said airtight container. Here, the oxygen concentration to be controlled in the airtight container is preferably in the range of 1 to 5% by volume, and the carbon dioxide concentration to be controlled in the airtight container is preferably in the range of 3 to 8% by volume, more preferably 5±1% by volume.

At this point, when the atmosphere control composition of the second embodiment further comprises the thermoplastic resin, the blended amount is preferably in the range of 35 to 300 parts by mass to 100 parts by mass of the ascorbic acid component, and more preferably in the range of 40 to 100 parts by mass.

Third Embodiment

Third embodiment of the atmosphere control composition of the present invention comprises, as described above, the transition metal catalyst as the ingredient (e) and additionally the carbonate salt as the ingredient (f) in the atmosphere control composition of the present invention.

More preferably, the atmosphere control composition of the present invention in the third embodiment described above comprises 100 parts by mass of the ascorbic acid component as the ingredient (a), 100 to 200 parts by mass, preferably 110 to 180 parts by mass of water as the ingredient (b), 50 to 400 parts by mass, preferably 75 to 300 parts by mass, more preferably 100 to 130 parts by weight of the porous carrier as the ingredient (c), 0.5 to 25 parts by mass, preferably 1.0 to 10 parts by mass, more preferably 1.0 to 5.0 parts by weight of the aldehyde-removing agent as the ingredient (d), 5 to 25 parts by mass, preferably 10 to 20 parts by weight of the transition metal catalyst as the ingredient (e), and 10 to 70 parts by mass, preferably 50 to 60 parts by weight of the carbonate salt as the ingredient (f), wherein the oxygen concentration in a gas impermeable airtight container may be adjusted to 12 to 18% by volume and the carbon dioxide concentration to 2 to 10% by volume by housing said composition into said airtight container. Here, the oxygen concentration to be controlled in the airtight container is preferably in the range of 13 to 18% by volume, more preferably in the range of 14 to 16% by volume and the carbon dioxide concentration to be controlled in the airtight container is preferably in the range of 3 to 8% by volume, more preferably 5±1% by volume.

At this point, when the atmosphere control composition of the third embodiment further comprises the thermoplastic resin, the blended amount is preferably in the range of 35 to 300 parts by mass to 100 parts by mass of the ascorbic acid component, and more preferably in the range of 100 to 200 parts by mass.

[Atmosphere Control Package]

The atmosphere control composition can also be packaged with a packaging material totally or partly containing an air permeable packaging material to prepare an atmosphere control package.

(Packaging Material)

The packaging material includes the one in the shape of a pouch made with two sheets of the air permeable packaging material bonded together, the one in the shape of a pouch made with a sheet of the air permeable packaging material and a sheet of the air impermeable packaging material bonded together, and the one in the shape of a pouch made by doubling a sheet of the air permeable packaging material and sealing the fringes other than the doubled part.

Here, when the air permeable packaging material and the air impermeable packaging material are quadrilateral, the packaging material includes the one in the shape of a pouch made by superposing two sheets of the air permeable packaging material and heat sealing the four sides, the one in the shape of a pouch made by superposing a sheet of the air permeable packaging material and a sheet of the air impermeable packaging material and heat sealing the four sides, and the one in the shape of a pouch made by doubling a sheet of the air permeable packaging material and heat sealing the three fringes other than the doubled part. In addition, the packaging material may also be the one in the shape of a pouch made by rolling the air permeable packaging material into a cylinder, of which both ends and trunk part are heat sealed.

(Air Permeable Packaging Material)

Packaging materials permeable by oxygen and carbon dioxide are selected as the air permeable packaging material. Among others, packaging materials having air resistance with a Gurley tester in the range of 600 sec or less, more preferably 90 sec or less are appropriately used. In this connection, air resistance shall be considered as the value measured by the method of JIS P8117-1998. More specifically, it refers to the time required to 100 ml of air to permeate the air permeable packaging material by using a Gurley densomer.

As the air permeable packaging material, there can be used paper, unwoven fabrics, and the following plastic films having air permeability conferred thereon. That is, there can be used as the plastic film a laminated film that a film including, for example, polyethylene terephthalate, polyamide, polypropylene, polycarbonate or the like and as a sealing layer a film including polyethylene, an ionomer, polybutadiene, an ethylene-acrylic acid copolymer, an ethylene-methacrylic acid copolymer or an ethylene-vinyl acetate copolymer or the like are laminate bonded. In addition, these laminated products can be used as the air permeable packaging material.

As the method for affording air permeability, a variety of methods including puncture processing with a needle or a heated needle can be employed. When air permeability is afforded by the puncture processing, the air permeability can be freely adjusted by the diameter, number, material property and the like of the pores to be punctured.

Further, the laminated film has preferably a thickness in the range of 50 to 300 μm, particularly in the range of 60 to 250 μm. In this case, a packaging material maintaining the strength and excellent in the heat seal property and the packaging aptitude can be provided as compared with the case that the thickness is out of the range described above.

The atmosphere control package is preferably received in a gas impermeable container or pouch before use and taken out of the gas impermeable container or pouch in time of use in order to maintain the function for a long period. In addition, when the atmosphere control package is used for the cell culture, the package is preferably subjected to sterilization with γ (gamma) ray and the like beforehand.

[Method for Culturing Cells]

The method for culturing cells of the present invention is the cell culture in which a culture vessel having an atmosphere control package, the cells and a culture medium received therein is placed within a gas impermeable airtight container, and the cells are cultured by adjusting the carbon dioxide concentration within the airtight container to the range of 2 to 10% by volume, preferably 3 to 8% by volume. In addition, the culturing temperature is preferably in the range of 20 to 45° C., particularly in the range of 25 to 40° C.

In the method for culturing cells of the present invention, the atmosphere within the gas impermeable container is not required specifically to be controlled, and, for example, air may be used. When the method for culturing cells of the present invention is carried out by filling air within the gas impermeable container and by using the atmosphere control composition (preferably, the composition of the third embodiment) which generates carbon dioxide volume equivalent to that of oxygen absorbed, the oxygen concentration will be in the range of about 11 to 19% by volume at the carbon dioxide concentration in the range of 2 to 10% by volume, and the oxygen concentration will be in the range of about 13 to 18% by volume at the carbon dioxide concentration in the range of 3 to 8% by volume.

In this connection, the oxygen concentration is not specifically limited in the method for culturing cells with the gas atmosphere control agent of the present invention. The usual cell culture is carried out with a carbon dioxide gas incubator and the like by selecting the carbon dioxide concentration within the incubator to about 5% by volume. On this occasion, if the oxygen concentration is not directly controlled, an atmosphere having the oxygen concentration in the range of 19 to 20% by volume will be formed along with the increase of the carbon dioxide concentration in air. However, the appropriate condition of the cell culture depends on the kinds of the cells, the oxygen concentration in addition to the carbon dioxide concentration may influence the culture showings. Besides, it is required in the academic studies that the response of the cells under the special atmospheres according to the gas atmosphere of the living body oxygen concentration is also examined. Thus, it is desirable to conduct the culture under the oxygen concentration suitable to the object also in the method for culturing cells of the present invention by appropriately controlling the blended amount of the respective ingredients in the atmosphere control composition. By way of example, if it is desired to conduct the culture in a much lower oxygen concentration without affecting the carbon dioxide concentration, an atmosphere control composition that the alkaline earth metal hydroxides and the like are blended to suppress the generation of carbon dioxide may be used for culture. It is also possible, for example, to further decrease the oxygen concentration while maintaining the carbon dioxide concentration within the gas impermeable container having air filled therein for adjusting the oxygen concentration to the range of about 1 to 7% by volume with the composition of the second embodiment or the oxygen concentration to the range of 0.1% by volume or less with the composition of the first embodiment.

As the specific example that the cell culture under the low oxygen condition is recommended, Japanese Patent Laid-Open Publication No. 2007-267701 discloses that the immature egg and the embryo fertilized in vitro are cultured under the oxygen atmosphere of 15% by volume and 5% by volume, respectively. Japanese Patent Laid-Open Publication No. 2007-312656 also discloses that the CHO (Chinese hamster ovary) cells are cultured under the oxygen atmosphere in the range of 5 to 10% by volume in order to improve the efficiency of gene amplification. In addition, the experiments of ischemia or ischemia reperfusion for examining at the cellular level the damages of individual organ or apparatus which is in the ischemic state caused by the lack of blood in operation, cardiac arrest, organ transplant and the like are performed under the oxygen atmosphere in the range of 0.1% by volume or less. Furthermore, the interior of carcinoma cells is under the lower oxygen atmosphere as compared with that of normal cells, and thus the culture of carcinoma cells are generally performed under the oxygen atmosphere in the range of 1 to 2% by volume for the studies of carcinoma under this gas atmosphere. More recently, it has been described that the efficiency for establishing the iPS cells is improved under the oxygen condition of 5% by volume (Yoshida Y, et al. Hypoxia enhances the generation of induced pluripotent stem cells. Cell Stem Cell. 2009; 5: 237-41).

As the method for receiving the cells and the culture medium in the culture vessel, any method such as the one for receiving a culture medium in which cells have been preliminarily seeded in a culture vessel and the one for receiving only a culture medium in a culture vessel before seeding cells in the culture medium can be adopted according to the kinds of the cells and culture mediums to be used. In addition, the culture mediums are not specifically limited and the ones usually used can be directly applied, so that the medium appropriate to the cells to be cultured can be selected freely.

(Gas Impermeable Airtight Container)

The gas impermeable airtight container in the method for culturing cells is the one which prevents the ventilation of a gas through the container and maintains the concentration of the oxygen and carbon dioxide formed with the atmosphere control agent projected into the container for a long period. The containers composed of glass, metals and plastics such as polycarbonate are generally used, but it is also possible to use a gas impermeable film and a laminate thereof.

(Cells)

While the cells used in the method for culturing cells are not specifically limited, the present invention can be particularly suitably employed in the culture of cells which are poor in resistance to aldehyde. The cells include microbial cells, animal cells, plant cells and insect cells, preferably microbial cells, animal cells, further preferably animal cells. Besides, suitable culturing gas atmospheres vary depending on the kinds of cells, but the interior of the gas impermeable airtight container can be maintained in a suitable gas atmosphere by appropriately controlling the blended amount of each compound in the atmosphere control composition.

(Culture Vessel)

The culture vessel used in the method for culturing cells is not specifically limited provided that the air permeability to the exterior is secured, and any vessel suitable for culture on the basis of volume, shape, material properties and the like can be used. Besides, the culture vessel having a cover can preferably be used, but it is also necessary in this case to secure the air permeability to the exterior of the vessel.

The method for culturing cells can be carried out by placing the atmosphere control package together with a culture vessel having the cells and the culture medium received therein within the gas impermeable airtight container before sealing the container and leaving the sealed container at a temperature suitable for culturing cells. In this occasion, an open type container having distilled water received therein may be also placed within the gas impermeable airtight container airtight for the purpose of measuring the produced amount of the aldehyde generated within the container and controlling the humidity within the container. The open type container includes a beaker and a flask in addition to the culture vessel, which is preferably the container similar to the one having the cells and the culture medium received therein.

In the method for culturing cells of the present invention, it is possible to conduct the microscopic observation and transport of the cells and tissues under a suitable gas atmosphere without the use of a gas bomb and a gas controller thereof by placing the atmosphere control package together with a culture vessel having the cells and the culture medium received therein within the gas impermeable airtight container before sealing the container and maintaining the airtight state.

Furthermore, in the present invention, the aldehyde concentration fused into the culture medium is controlled preferably in the range of 2 mg/l or less, more preferably 1.5 mg/l or less, further preferably 1.0 mg/l or less, which is suitable for the cell culturing condition.

EXAMPLES

The present invention is now described in detail with reference to examples, but the present invention is not limited thereto.

In the following examples, comparative examples and referential examples, the terms "cell", "culture medium" and "culture vessel" described below were used. In addition, the concentration of aldehyde was measured by the following measurement method.

(1. Cell)

All of the cells were the ones sold in lots from Health Science Research Resources Bank. The cells used are shown in Table 1.

TABLE 1

|  | Cell types | Resource No. | Lot No. |
|---|---|---|---|
| Tig-3-20 | Human fetal lung derived cells | JCRB0506 | R034 |
| HEK293 | Human embryonic kidney derived cells | JCRB9068 | 12272004 |
| A549 | Human pulmonary adenocarcinoma derived cells | JCRB0076 | 7262006 |
| HeLa | Human cervical cancer derived cells | JCRB9004 | 7312008 |
| A431 | Human epithelial cancer derived cells | JCRB9009 | F00954 |

(2. Culture Medium)

MEM culture medium (product name; Invitrogen GIBCO 11095-080 Minimum Essential Medium, containing liquid Earle salt);

D-MEM culture medium (product name; Invitrogen GIBCO 11965-092 Dulbecco's Modified Eagle Medium liquid, high glucose (4,500 mg/l));

MEM non-essential amino acid solution (product name; Invitrogen GIBCO 11140-050); and Fetal bovine serum FBS (product name; Invitrogen GIBCO 12483-020 Qualified Fetal Bovine Serum, Canada).

(3. Culture Vessel)

60 mm diameter dish (product name; AGC Techno Glass IWAKI 3010-060 60 mm/Tissue Culture Dish)

(Method for Measuring Aldehyde Concentration (MBTH Method))

This method is a colorimetric method with use of the color reaction of 3-methyl-2-benzothiazolinone hydrazone, and the aldehyde concentration in distilled water was measured by the following procedure with use of "Water Quality Test Reagent Set No. 51 LR-FOR" Kyoritsu Chemical-Check Lab., Corp.

1. Aldehyde containing distilled water obtained in examples or comparative examples was appropriately diluted to a measurable concentration of 25 ml, to which one pack of the R-1 reagent was added and left standing with stirring for 10 minutes.

2. Two drops of the R-2 reagent was added and left standing with stirring for 5 minutes.

3. Absorbance at 625 nm was measured with a spectrophotometer ("UV-1200" manufactured by Shimadzu Corporation) to determine the aldehyde concentration.

[Effect of Aldehyde-Removing Agent]

Referential Example 1

Three 60 mm diameter dishes containing an MEM medium having 5 ml of a 10% FBS added thereto and having Tig-3-20 seeded at a cell density of $2.0 \times 10^4$/ml were loaded in a carbon dioxide gas incubator which was set up at 5% by volume of carbon dioxide. After culture at 37° C. for three days, the cell count was measured. The result and the concentrations of oxygen and carbon dioxide in the airtight container after culture are shown in Table 2. The cell count after three days increased to about six times.

Example 1

Into 90 g of an aqueous solution of sodium L-ascorbate (concentration: 45% by weight) were dissolved 6 g of ferrous sulfate·7 hydrate salt and 0.5 g of ethylene urea and the aqueous solution was impregnated into 50 g of granular activated carbon, after which 70 g of a low molecular weight polyethylene and 20 g of sodium carbonate were added and mixed to give the atmosphere control composition A1 in which ethylene urea was blended (in an amount of 1.2 parts by mass to 100 parts by mass of sodium L-ascorbate).

One sheet of Japanese paper having a porous polyethylene film laminated thereon was bended so as the polyethylene side to be in the inside, and the two sides except the bended part were heat sealed to give an air permeable packaging material in the shape of a pouch having a length 90 mm×width 55 mm (air resistance: 8 sec by the Gurley tester method), into which 5 g of the atmosphere control composition A1 was filled, the remaining side except the bended part was heat sealed to give the atmosphere control package A2 in which ethylene urea was blended.

The atmosphere control package A2 subjected to sterilization with γ ray and two 60 mm diameter dishes containing 5 ml of distilled water were loaded in a 2500 ml volume polycarbonate gas impermeable airtight container. After left standing at 37° C. for three days, the aldehyde concentration transferred into the distilled water was measured by the MBTH method. In addition, the atmosphere control package A2 and three 60 mm diameter dishes containing an MEM medium having 5 ml of a 10% FBS added thereto and having human fetal lung derived cells (referred to hereinafter as Tig-3-20) seeded at a cell density of $2.0 \times 10^4$/ml were loaded in a 2500 ml volume polycarbonate gas impermeable airtight container. After culture at 37° C. for three days, the cell count was measured.

The result and the concentrations of oxygen and carbon dioxide in the airtight container after culture are shown in Table 2. The cell count after three days was approximately on the same level as the case cultured in the carbon dioxide incubator.

Example 2

After obtaining the atmosphere control composition B1 having ethylene urea (in an amount of 2.5 parts by mass to 100 parts by mass of sodium L-ascorbate) blended thereto in the same manner as in Example 1 except the blended amount of ethylene urea was adjusted to 1.0 g, the atmosphere control package B2 having ethylene urea blended thereto was obtained in the same manner as in Example 1. Next, the test for measuring the aldehyde concentration in distilled water and the cell culture test were carried out in the same manner as in Example 1.

The results are shown in Table 2. The cell count after culture for three days was approximately on the same level as the case cultured in the carbon dioxide incubator.

Example 3

After obtaining the atmosphere control composition C1 having ethylene urea (in an amount of 4.9 parts by mass to 100 parts by mass of sodium L-ascorbate) blended thereto in the same manner as in Example 1 except the blended amount of ethylene urea was adjusted to 2.0 g, the atmosphere control package C2 having ethylene urea blended thereto was obtained in the same manner as in Example 1. Next, the test for measuring the aldehyde concentration in distilled water and the cell culture test were carried out in the same manner as in Example 1.

The results are shown in Table 2. The cell count after culture for three days was approximately on the same level as the case cultured in the carbon dioxide incubator.

Example 4

After obtaining the atmosphere control composition D1 having ethylene urea (in an amount of 25 parts by mass to 100 parts by mass of sodium L-ascorbate) blended thereto in the same manner as in Example 1 except the blended amount of ethylene urea was adjusted to 10 g, the atmosphere control package D2 having ethylene urea blended thereto was obtained in the same manner as in Example 1. Next, the test for measuring the aldehyde concentration in distilled water and the cell culture test were carried out in the same manner as in Example 1.

The results are shown in Table 2. The cell count after culture for three days was approximately on the same level as the case cultured in the carbon dioxide incubator.

Example 5

After obtaining the atmosphere control composition E1 having ethylene urea (in an amount of 4.9 parts by mass to 100 parts by mass of sodium L-ascorbate) blended thereto in the same manner as in Example 1 except 2.0 g of urea was blended in place of ethylene urea, the atmosphere control package E2 having arginine blended thereto was obtained in the same manner as in Example 1. Next, the test for measuring the aldehyde concentration in distilled water and the cell culture test were carried out in the same manner as in Example 1.

The results are shown in Table 2. The cell count after culture for three days was approximately on the same level as the case cultured in the carbon dioxide incubator.

Example 6

After obtaining the atmosphere control composition F1 having arginine (in an amount of 4.9 parts by mass to 100 parts by mass of sodium L-ascorbate) blended thereto in the same manner as in Example 1 except 2.0 g of arginine was blended in place of ethylene urea, the atmosphere control package F2 having arginine blended thereto was obtained in the same manner as in Example 1. Next, the test for measuring the aldehyde concentration in distilled water and the cell culture test were carried out in the same manner as in Example 1.

The results are shown in Table 2. The cell count after culture for three days was approximately on the same level as the case cultured in the carbon dioxide incubator.

Example 7

After obtaining the atmosphere control composition G1 having lysine (in an amount of 4.9 parts by mass to 100 parts by mass of sodium L-ascorbate) blended thereto in the same manner as in Example 1 except 2.0 g of lysine hydrochloride was blended in place of ethylene urea, the atmosphere control package G2 having lysine hydrochloride blended thereto was obtained in the same manner as in Example 1. Next, the test for measuring the aldehyde concentration in distilled water and the cell culture test were carried out in the same manner as in Example 1.

The results are shown in Table 2. The cell count after culture for three days was approximately on the same level as the case cultured in the carbon dioxide incubator.

Example 8

36.0 g of L-ascorbic acid, 8 g of sodium hydroxide, 10.0 g of polyallylamine (product name; PAA-03, 20% aqueous solution, average molecular weight: 3000, manufactured by Nitto Boseki Co., Ltd.), 6 g of ferrous sulfate·7 hydrate and 38.0 g of water were blended to prepare a 45% aqueous solution of sodium L-ascorbate containing the polyallylamine. After impregnating the aqueous solution in 50 g of granular activated carbon, 70 g of low molecular weight polyethylene and 20 g of sodium carbonate were added and blended to give the atmosphere control composition H1 having the polyallylamine (in an amount of 4.9 parts by mass to 100 parts by mass of sodium L-ascorbate) blended thereto. After the atmosphere control package H2 was prepared hereinafter in the same manner as in Example 3, the test for measuring the aldehyde concentration in distilled water and the cell culture test were carried out with this package.

The results are shown in Table 2. The cell count after culture for three days was approximately on the same level as the case cultured in the carbon dioxide incubator.

Comparative Example 1

After obtaining the atmosphere control composition I1 having aminoguanidine sulfate (in an amount of 4.9 parts by mass to 100 parts by mass of sodium L-ascorbate) blended thereto in the same manner as in Example 1 except 2.0 g of aminoguanidine sulfate was blended in place of ethylene urea, the atmosphere control package I2 having aminoguanidine sulfate blended thereto was obtained in the same manner as in Example 1. Next, the test for measuring the aldehyde concentration in distilled water and the cell culture test were carried out in the same manner as in Example 1.

The results are shown in Table 2. The cell count after three days was lesser as compared with the case cultured in the carbon dioxide incubator.

Comparative Example 2

After obtaining the atmosphere control composition J1 having p-aminobenzenesulfonic acid (in an amount of 2.5 parts by mass to 100 parts by mass of sodium L-ascorbate) blended thereto in the same manner as in Example 1 except 1.0 g of p-aminobenzenesulfonic acid was blended in place of ethylene urea, the atmosphere control package J2 having p-aminobenzenesulfonic acid blended thereto was obtained in the same manner as in Example 1. Next, the test for measuring the aldehyde concentration in distilled water was carried out in the same manner as in Example 1.

The results are shown in Table 2. It was observed that the aldehyde-removing effect was lower as compared with those of the other aldehyde-removing agents.

Comparative Example 3

After obtaining the atmosphere control composition K1 having ammonium sulfate (in an amount of 25 parts by mass to 100 parts by mass of sodium L-ascorbate) blended thereto in the same manner as in Example 1 except 10.0 g of ammonium sulfate was blended in place of ethylene urea, the atmosphere control package K2 having ammonium sulfate blended thereto was obtained in the same manner as in Example 1. Next, the test for measuring the aldehyde concentration in distilled water and the cell culture test were carried out in the same manner as in Example 1.

The results are shown in Table 2. While the aldehyde concentration was low, irritant odor was generated from the agent and the cell count after three days was lesser as compared with the case cultured in the carbon dioxide incubator.

Comparative Example 4

After obtaining the atmosphere control composition N1 in the same manner as in Example 1 except ethylene urea was not blended, the atmosphere control package N2 was obtained in the same manner as in Example 1. Next, the test for measuring the aldehyde concentration in distilled water and the cell culture test were carried out in the same manner as in Example 1.

The results are shown in Table 2. The cell count after three days was lesser as compared with the case with use of the carbon dioxide incubator.

On the other hand, the aldehyde concentration could not be reduced in Comparative Examples 1 and 2. Furthermore, Comparative Example 3, the aldehyde concentration could be reduced, but the cell density was in a lower level as compared with results in Examples.

[Effect of Aldehyde-Removing Agent in Different Oxygen Concentrations]

Example 9

In the same manner as in Example 3, the atmosphere control composition C1 and the atmosphere control package C2 were prepared. In the same manner as in Example 3, the test for measuring the aldehyde concentration in distilled water was conducted.

Example 10

Into 123 g of an aqueous solution of sodium L-ascorbate (concentration: 45% by weight) was dissolved 2.7 g of ethylene urea and the aqueous solution was impregnated into 50 g of granular activated carbon, after which 29 g of a low molecular weight polyethylene and 23 g of magnesium hydroxide were added and mixed to give the atmosphere control composition L1 in which ethylene urea was blended (in an amount of 4.9 parts by mass to 100 parts by mass of sodium L-ascorbate).

One sheet of Japanese paper having a porous polyethylene film laminated thereon was bended so as the polyethylene side to be in the inside, and the two sides except the bended part were heat sealed to give an air permeable packaging material in the shape of a pouch having a length 90 mm×width 55 mm (air resistance: 8 sec by the Gurley tester method), into

TABLE 2

| | Aldehyde-removing agent | Blended amount of aldehyde-removing agent*[1] (part by mass) | Concentration of aldehyde (mg/l) | Cell density after culture (cells/ml) | Oxygen concentration (%) | Carbon dioxide concentration (%) |
|---|---|---|---|---|---|---|
| Referential Example 1 | — | — | — | $1.2 \times 10^5$ | 19.9 | 5.0 |
| Example 1 | Ethylene urea | 1.2 | 0.88 | $1.2 \times 10^5$ | 14.2 | 6.2 |
| Example 2 | Ethylene urea | 2.5 | 0.58 | $1.3 \times 10^5$ | 14.7 | 5.8 |
| Example 3 | Ethylene urea | 4.9 | 0.37 | $1.1 \times 10^5$ | 14.1 | 6.2 |
| Example 4 | Ethylene urea | 25 | 0.20 | $1.2 \times 10^5$ | 14.8 | 5.9 |
| Example 5 | Urea | 4.9 | 1.09 | $1.2 \times 10^5$ | 14.0 | 5.7 |
| Example 6 | Arginine | 4.9 | 1.46 | $1.2 \times 10^5$ | 14.1 | 5.7 |
| Example 7 | Lysine hydrochloride | 4.9 | 1.12 | $1.3 \times 10^5$ | 15.2 | 4.8 |
| Example 8 | Polyallylamine | 4.9 | 0.47 | $1.3 \times 10^5$ | 13.3 | 6.4 |
| Comparative Example 1 | Aminoguanidine sulfate | 4.9 | 3.48 | $3.2 \times 10^4$ | 13.4 | 6.2 |
| Comparative Example 2 | p-Aminobenzenesulfonic acid | 2.5 | 3.46 | No culture | 14.4 | 5.2 |
| Comparative Example 3 | Ammonium sulfate | 25 | 3.46 | $4.4 \times 10^4$ | 14.1 | 5.9 |
| Comparative Example 4 | — | 0 | 4.5 | $4.2 \times 10^4$ | 13.6 | 5.9 |

*[1]Blended amount to 100 parts by mass of sodium L-ascorbate

As is apparent from Examples 1 to 8, the atmosphere control composition of the present invention can suppress the generation of aldehyde without affecting the oxygen absorption ability and the carbon dioxide generation ability inherently existing in the atmosphere control agent, and the cell density after culture was also approximately on the same level as the case cultured in the carbon dioxide incubator in Referential Example.

which 12 g of the atmosphere control composition L1 was filled, the remaining side except the bended part was heat sealed to give the atmosphere control package L2 in which ethylene urea was blended.

The atmosphere control package L2 subjected to sterilization with γ ray and two 60 mm diameter dishes containing 5 ml of distilled water were loaded in a 2500 ml volume polycarbonate gas impermeable airtight container. After left standing at 37° C. for three days, the aldehyde concentration transferred into the distilled water was measured by the MBTH method.

The results are shown in Table 4. Aldehyde was suppressed to the concentration of 0.36 mg/l without influencing the controllability of both the oxygen concentration and the carbon dioxide concentration.

Example 11

Into 90 g of an aqueous solution of sodium L-ascorbate (concentration: 45% by weight) were dissolved 6 g of ferrous sulfate·7 hydrate salt and 2 g of ethylene urea and the aqueous solution was impregnated into 50 g of granular activated carbon, after which 42 g of a low molecular weight polyethylene, 2 g of magnesium hydroxide and 12 g of calcium hydroxide were added and mixed to give the atmosphere control composition M1 in which ethylene urea was blended (in an amount of 4.9 parts by mass to 100 parts by mass of sodium L-ascorbate).

One sheet of Japanese paper having a porous polyethylene film laminated thereon was bended so as the polyethylene side to be in the inside, and the two sides except the bended part were heat sealed to give an air permeable packaging material in the shape of a pouch having a length 90 mm×width 55 mm (air resistance: 8 sec by the Gurley tester method), into which 30 g of the atmosphere control composition A1 was filled, the remaining side except the bended part was heat sealed to give the atmosphere control package M2 in which ethylene urea was blended.

The atmosphere control package M2 subjected to sterilization with γ ray and two 60 mm diameter dishes containing 5 ml of distilled water were loaded in a 2500 ml volume polycarbonate gas impermeable airtight container. After left standing at 37° C. for three days, the aldehyde concentration transferred into the distilled water was measured by the MBTH method.

The results are shown in Table 4. Aldehyde was suppressed to the concentration of 0.58 mg/l without influencing the controllability of both the oxygen concentration and the carbon dioxide concentration.

Examples 11b to 11d

The atmosphere control composition and the atmosphere control package were prepared in the same manner as in Example 11 except the respective added amounts of magnesium hydroxide and calcium hydroxide were changed into those of Table 3, and further the measurement of the aldehyde concentration was conducted.

The results are shown in Table 4.

TABLE 3

|  | Magnesium hydroxide (g) | Calcium hydroxide (g) |
| --- | --- | --- |
| Example 11b | 1.2 | 12 |
| Example 11c | 0.8 | 12 |
| Example 11d | 1.2 | 14 |

TABLE 4

|  | Aldehyde-removing agent | Blended amount of aldehyde-removing agent*[1] (part by mass) | Concentration of aldehyde (mg/l) | Oxygen concentration (%) | Carbon dioxide concentration (%) |
| --- | --- | --- | --- | --- | --- |
| Example 9 | Ethylene urea | 4.9 | 0.37 | 14.1 | 6.2 |
| Example 10 | Ethylene urea | 4.9 | 0.36 | 4.0 | 4.7 |
| Example 11 | Ethylene urea | 4.9 | 0.58 | 0.001 | 5.1 |
| Example 11b | Ethylene urea | 4.9 | 0.43 | 0.001 | 5.5 |
| Example 11c | Ethylene urea | 4.9 | 0.50 | 0.001 | 5.9 |
| Example 11d | Ethylene urea | 4.9 | 0.40 | 0.001 | 4.2 |

*[1]Blended amount to 100 parts by mass of sodium L-ascorbate

As is apparent from Examples 9 to 11 and Examples 11b to 11d, the generation of aldehyde was successfully suppressed by the atmosphere control composition of the present invention in a variety of oxygen concentration without affecting the oxygen absorption ability and the carbon dioxide generation ability inherently existing in the atmosphere control agent.

[Confirmation of the Aldehyde-removing Effect in Different Cells]

Referential Example 2

In the same manner as in Referential Example 1 except the human embryonic kidney derived cells (referred to hereinafter as HEK293) was used in place of Tig-3-20, after culture at 37° C. for three days, the cell count was measured.

The results are shown together with the oxygen concentration and the carbon dioxide concentration in the airtight container after the cell culture in Table 5. The cell count after three days increased to about 1.5 times.

Example 12

The aldehyde concentration transferred into distilled water and the cell count after culture at 37° C. for three days were measured in the same manner as in Example 3 except HEK293 was used in place of Tig-3-20.

The results are shown together with the oxygen concentration and the carbon dioxide concentration in the airtight container after the cell culture in Table 5. The cell count after three days was approximately on the same level as the case cultured in the carbon dioxide incubator.

Comparative Example 5

The aldehyde concentration transferred into distilled water and the cell count after culture at 37° C. for three days were measured in the same manner as in Comparative Example 4 except HEK293 was used in lieu of Tig-3-20.

The results are shown together with the oxygen concentration and the carbon dioxide concentration in the airtight container after the cell culture in Table 5. The cells were almost extinct.

The results are shown together with the oxygen concentration and the carbon dioxide concentration in the airtight container after the cell culture in Table 6. The cell count after three days was approximately on the same level as the case cultured in the carbon dioxide incubator.

Comparative Example 6

The aldehyde concentration transferred into distilled water and the cell count after culture at 37° C. for three days were determined in the same manner as in Comparative Example 4 except A549 was used in place of Tig-3-20 and the same culture medium as in Referential Example 3 was used.

TABLE 5

|  | Cell type | Concentration of aldehyde (mg/l) | Cell seeding density (cells/ml) | Cell density after culture (cells/ml) | Oxygen concentration (%) | Carbon dioxide concentration (%) |
|---|---|---|---|---|---|---|
| Referential Example 2 | HEK293 Human embryonic kidney derived cells | — | $2.0 \times 10^4$ | $3.4 \times 10^4$ | 19.9 | 5.0 |
| Example 12 |  | 0.37 |  | $3.0 \times 10^4$ | 13.9 | 6.0 |
| Comparative Example 5 |  | 4.5 |  | $2.4 \times 10^3$ | 14.3 | 5.4 |

The results are shown together with the oxygen concentration and the carbon dioxide concentration in the airtight container after the cell culture in Table 6. The cell count after three days was lesser as compared with the case of the culture with the carbon dioxide incubator.

TABLE 6

|  | Cell type | Concentration of aldehyde (mg/l) | Cell seeding density (cells/ml) | Cell density after culture (cells/ml) | Oxygen concentration (%) | Carbon dioxide concentration (%) |
|---|---|---|---|---|---|---|
| Referential Example 3 | A549 Human pulmonary adenocarcinoma derived cells | — | $2.0 \times 10^4$ | $1.3 \times 10^5$ | 19.9 | 5.0 |
| Example 13 |  | 0.37 |  | $1.4 \times 10^5$ | 14.3 | 5.6 |
| Comparative Example 6 |  | 4.5 |  | $7.4 \times 10^4$ | 14.2 | 5.6 |

Referential Example 3

After culture at 37° C. for three days in the same manner as in Referential Example 1 except the human pulmonary adenocarcinoma derived cells (referred to hereinafter as A549) was used in place of Tig-3-20 and the MEM culture medium having 10% FBS and 0.1 mM of non-essential amino acids added thereto in place of the MEM culture medium having 10% FBS added thereto, the cell count was measured.

The results are shown together with the oxygen concentration and the carbon dioxide concentration in the airtight container after the cell culture in Table 5. The cell count after three days increased to about 6.5 times.

Example 13

The aldehyde concentration transferred into distilled water and the cell count after culture at 37° C. for three days were determined in the same manner as in Example 3 except A549 was used in place of Tig-3-20 and the same culture medium as in Referential Example 3 was used.

Referential Example 4

The cell count was determined after culture at 37° C. for three days in the same manner as in Referential Example 1 except human cervical cancer derived cells (referred to hereinafter as HeLa) were used in place of Tig-3-20 and the MEM culture medium having 10% FBS and 0.1 mM of non-essential amino acids added thereto in place of the MEM culture medium having 10% FBS added thereto and the cell seeding density was set up at $1.0 \times 10^4$ cell/ml.

The results are shown together with the oxygen concentration and the carbon dioxide concentration in the airtight container after the cell culture in Table 7. The cell count after three days increased to about 3 times.

Example 14

The aldehyde concentration transferred into distilled water and the cell count after culture at 37° C. for three days were determined in the same manner as in Example 3 except HeLa was used in place of Tig-3-20 and the cell seeding density was set up at $1.0 \times 10^4$ cells/ml.

The results are shown together with the oxygen concentration and the carbon dioxide concentration in the airtight container after the cell culture in Table 7. The cell count after three days was approximately on the same level as the case cultured in the carbon dioxide incubator.

Comparative Example 7

The aldehyde concentration transferred into distilled water and the cell count after culture at 37° C. for three days were determined in the same manner as in Comparative Example 4 except HeLa was used in place of Tig-3-20, the same culture medium as in Referential Example 4 was used and the cell seeding density was set up at $1.0 \times 10^4$ cell/ml.

The results are shown together with the oxygen concentration and the carbon dioxide concentration in the airtight container after the cell culture in Table 7. The cell count after three days was lesser as compared with the case of the culture with the carbon dioxide incubator.

Referential Example 5 was used and the cell seeding density was set up at $1.0 \times 10^4$ cells/ml.

The results are shown together with the oxygen concentration and the carbon dioxide concentration in the airtight container after the cell culture in Table 8. The cell count after three days was approximately on the same level as the case cultured in the carbon dioxide incubator.

Comparative Example 8

The aldehyde concentration transferred into distilled water and the cell count after culture at 37° C. for three days were determined in the same manner as in Comparative Example 4 except A431 was used in place of Tig-3-20, the same culture medium as in Referential Example 5 was used and the cell seeding density was set up at $1.0 \times 10^4$ cell/ml.

TABLE 7

| | Cell type | Concentration of aldehyde (mg/l) | Cell seeding density (cells/ml) | Cell density after culture (cells/ml) | Oxygen concentration (%) | Carbon dioxide concentration (%) |
|---|---|---|---|---|---|---|
| Referential Example 4 | HeLa Human cervical carcinoma derived cells | — | $1.0 \times 10^4$ | $2.8 \times 10^4$ | 19.9 | 5.0 |
| Example 14 | | 0.37 | | $4.8 \times 10^4$ | 14.4 | 5.7 |
| Comparative Example 7 | | 4.5 | | $1.1 \times 10^4$ | 14.4 | 5.5 |

The results are shown together with the oxygen concentration and the carbon dioxide concentration in the airtight container after the cell culture in Table 7. The cell count after three days was lesser as compared with the case of the culture with the carbon dioxide incubator.

TABLE 8

| | Cell type | Concentration of aldehyde (mg/l) | Cell seeding density (cells/ml) | Cell density after culture (cells/ml) | Oxygen concentration (%) | Carbon dioxide concentration (%) |
|---|---|---|---|---|---|---|
| Referential Example 5 | A431 Human epithelial carcinoma derived cells | — | $1.0 \times 10^4$ | $2.6 \times 10^4$ | 19.9 | 5.0 |
| Example 15 | | 0.37 | | $2.8 \times 10^4$ | 14.0 | 5.9 |
| Comparative Example 8 | | 4.5 | | $8.0 \times 10^3$ | 14.3 | 5.6 |

Referential Example 5

The cell count was determined after culture at 37° C. for three days in the same manner as in Referential Example 1 except human epthelial cancer derived cells (referred to hereinafter as A431) were used in place of Tig-3-20, the D-MEM culture medium having 10% FBS added thereto in place of the MEM culture medium having 10% FBS added thereto and the cell seeding density was set up at $1.0 \times 10^4$ cell/ml.

The results are shown together with the oxygen concentration and the carbon dioxide concentration in the airtight container after the cell culture in Table 8. The cell count after three days increased to about 2.5 times.

Example 15

The aldehyde concentration transferred into distilled water and the cell count after culture at 37° C. for three days were determined in the same manner as in Example 3 except A431 was used in place of Tig-3-20, the same culture medium as in As is apparent from Tables 5 to 8, also in various cells other than Tig-3-20, the cell density after culture at least equivalent to the level achieved by the carbon dioxide gas incubator in Referential Examples could be achieved by the culture methods of the present invention in Examples. On the other hand, in Comparative Examples that no aldehyde-removing agent was blended, the cell density after culture was in low levels.

The atmosphere control agent according to the present invention makes possible to give a convenient and economic cell culture by which the result of cell culture equivalent to the case of the culture with the carbon dioxide gas incubator can be obtained.

The invention claimed is:
1. An atmosphere control composition for use in the culture of cells, comprising a blend of:
(a) an ascorbic acid component,
(b) water,
(c) a porous carrier,
(d) an aldehyde-removing agent, wherein said atmosphere control composition contains 0.5 to 25 parts by mass of the aldehyde-removing agent as the ingredient (d) based on 100 parts by mass of the ascorbic acid component (a), and (e) a transition metal catalyst and/or an alkaline earth metal hydroxide, wherein the aldehyde-removing agent is ethylene urea, urea, arginine, lysine hydrochloride or a polyallylamine.

2. The atmosphere control composition according to claim 1, wherein the ingredient (e) comprises a transition metal catalyst and at least two alkaline earth metal hydroxides.

3. The atmosphere control composition according to claim 2, wherein the alkaline earth metal hydroxides to be used are magnesium hydroxide and calcium hydroxide.

4. The atmosphere control composition according to claim 1, wherein said blend of (a), (b), (c) and (d) contains:

100 parts by mass of an ascorbic acid component as the ingredient (a), 100 to 200 parts by mass of water as the ingredient (b) based on 100 parts by mass of the ascorbic acid component, 50 to 400 parts by mass of a porous carrier as the ingredient (c) based on 100 parts by mass of the ascorbic acid component, and 5 to 25 parts by mass of a transition metal catalyst, 1 to 10 parts by mass of magnesium hydroxide and 20 to 40 parts by mass of calcium hydroxide as the ingredient (e) based on 100 parts by mass of the ascorbic acid component, wherein the oxygen concentration in a gas impermeable airtight container may be adjusted to the range of 0.1% by volume or less and the carbon dioxide concentration to the range of 2 to 10% by volume by housing said composition into said airtight container.

5. The atmosphere control composition according to claim 1, comprising only the alkaline earth metal hydroxides as the ingredient (e).

6. The atmosphere control composition according to claim 1, comprising 100 parts by mass of an ascorbic acid component as the ingredient (a), 100 to 200 parts by mass of water as the ingredient (b), 50 to 400 parts by mass of a porous carrier as the ingredient (c), 0.5 to 25 parts by mass of an aldehyde-removing agent as the ingredient (d), and 20 to 55 parts by mass of an alkaline earth metal hydroxide as the ingredient (e), wherein the oxygen concentration in a gas impermeable airtight container may be adjusted to the range of 1 to 7% by volume and the carbon dioxide concentration to the range of 2 to 10% by volume by housing said composition into said airtight container.

7. The atmosphere control composition according to claim 1, comprising a transition metal catalyst as the ingredient (e) and further a carbonate salt as the ingredient (f).

8. The atmosphere control composition according to claim 1, comprising 100 parts by mass of an ascorbic acid component as the ingredient (a), 100 to 200 parts by mass of water as the ingredient (b), 50 to 400 parts by mass of a porous carrier as the ingredient (c), 0.5 to 25 parts by mass of an aldehyde-removing agent as the ingredient (d), 5 to 25 parts by mass of a transition metal catalyst as the ingredient (e), and 10 to 70 parts by mass of a carbonate salt as the ingredient (f), wherein the oxygen concentration in a gas impermeable airtight container may be adjusted to 12 to 18% by volume and the carbon dioxide concentration to 2 to 10% by volume by housing said composition into said airtight container.

9. The atmosphere control composition according to claim 1, additionally comprising a thermoplastic resin.

10. The atmosphere control composition according to claim 1, wherein a porous carrier as the ingredient (c) is activated carbon.

11. An atmosphere control package which comprises packaging the atmosphere control composition according to claim 1, with a packaging material totally or partly containing an air permeable packaging material.

12. A method for culturing cells which comprises setting up the atmosphere control package according to claim 11 and a culture vessel having cells and a culture medium housed therein within a gas impermeable airtight container and thus culturing the cells by adjusting the carbon dioxide concentration in said airtight container to the range of 2 to 10% by volume.

13. The method for culturing cells according to claim 12, wherein the concentration of aldehyde fused into the culture medium is adjusted to the range of 2 mg/l or less.

* * * * *